US00PP21029P3

(12) United States Plant Patent
Meilland

(10) Patent No.: US PP21,029 P3
(45) Date of Patent: Jun. 1, 2010

(54) MINI SHRUB ROSE PLANT NAMED 'MEISILIMOND'

(50) Latin Name: *Rosa hybrida*
Varietal Denomination: Meisilimond

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 34 days.

(21) Appl. No.: 12/285,418

(22) Filed: Oct. 3, 2008

(65) Prior Publication Data

US 2010/0088789 P1 Apr. 8, 2010

(51) Int. Cl.
*A01H 5/00* (2006.01)

(52) U.S. Cl. ..... Plt./118

(58) Field of Classification Search ..... Plt./121, Plt./107, 118, 117, 104, 103
See application file for complete search history.

*Primary Examiner*—Kent L Bell
(74) *Attorney, Agent, or Firm*—Buchanan Ingersoll & Rooney PC

(57) ABSTRACT

A new and distinct variety of Mini Shrub Rose plant is provided that forms in abundance on a substantially continuous basis single blossoms that are light pink to white in coloration. The buds are pointed. The vegetation is vigorous and the growth habit is small low-growing, round, and bushy. The foliage is of an attractive light green coloration, bears a matte finish, and contrasts nicely with the light pink to white blossom coloration. The disease resistance is above average for the class with respect to Black Spot. The plant is particularly well suited for providing attractive ornamentation.

1 Drawing Sheet

Botanical/commercial classification: *Rosa hybrida*/Mini Shrub Rose Plant.

Varietal denomination: cv. Meisilimond.

SUMMARY OF THE INVENTION

The new variety of *Rosa hybrida* Mini Shrub Rose plant was created in France by artificial pollination wherein two parents were crossed which previously had been studied in the hope that they would contribute the desired characteristics. The female parent (i.e., the seed parent) was an unnamed and unreleased seedling (non-patented in the United States). The male parent (i.e., the pollen parent) was the 'Meineyta' variety. The 'Meineyta' variety is marketed under the CUMBA MEILLANDIA trademark.

The parentage of the new variety can be summarized as follows:

Unnamed Seedling×'Meineyta'

The seeds resulting from the above pollination were sown and small plants were obtained which were physically and biologically different from each other. Selective study resulted in the identification of a single plant of the new variety.

It was found that the new Mini Shrub Rose plant of the present invention:

(a) displays a small low-growing, round, and bushy growth habit, (b) forms vigorous vegetation, (c) forms on a substantially continuous basis attractive single blossoms that are light pink to white in coloration, (d) displays attractive light green foliage having a matte finish, (e) displays above average disease resistance to Black Spot, and (f) is particularly well suited for providing attractive ornamentation.

The new variety well meets the needs of the horticultural industry and can be grown to advantage in parks and gardens. It is well amenable for growing in small areas where an attractive small low-growing flowering plant is desired.

The new variety can be readily distinguished from its ancestors. For instance, the 'Meineyta' variety displays a more divergent growth habit and forms very double bicolored blossoms of orange-yellow. Also, when compared to the 'Meimarivon' variety (U.S. Plant Pat. No. 19,954), such variety forms double blossoms that are larger and are medium pink in coloration unlike those of the new variety.

The new variety has been found to undergo asexual propagation at Wasco, Calif., U.S.A., by a number of routes, including budding, grafting, and the use of cuttings. Such asexual propagation by the above-mentioned techniques has shown that the characteristics of the new variety are stable and are strictly transmissible by such asexual propagation from one generation to another. Accordingly, the new variety undergoes asexual propagation in a true-to-type manner.

The new variety has been named 'Meisilimond', and is being marketed under the SILICON VALLEY DIAMOND trademark.

BRIEF DESCRIPTION OF THE PHOTOGRAPH

The accompanying photographs show as nearly true as it is reasonably possible to make the same, in color illustrations of this character, typical specimens of the new variety. The illustrated plants were approximately two years of age and were being grown outdoors at Wasco, Calif., U.S.A.

DETAILED DESCRIPTION

Figure 1:
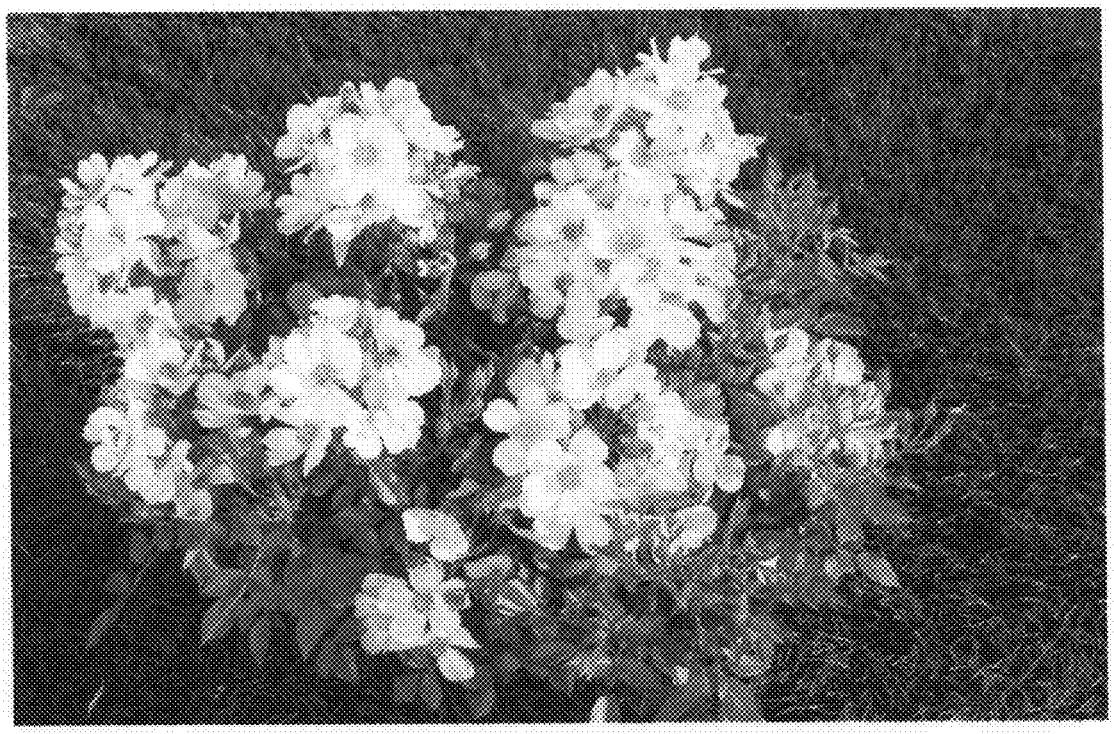
FIG. 1 shows a typical flowering plant of the new variety.
Figure 2:
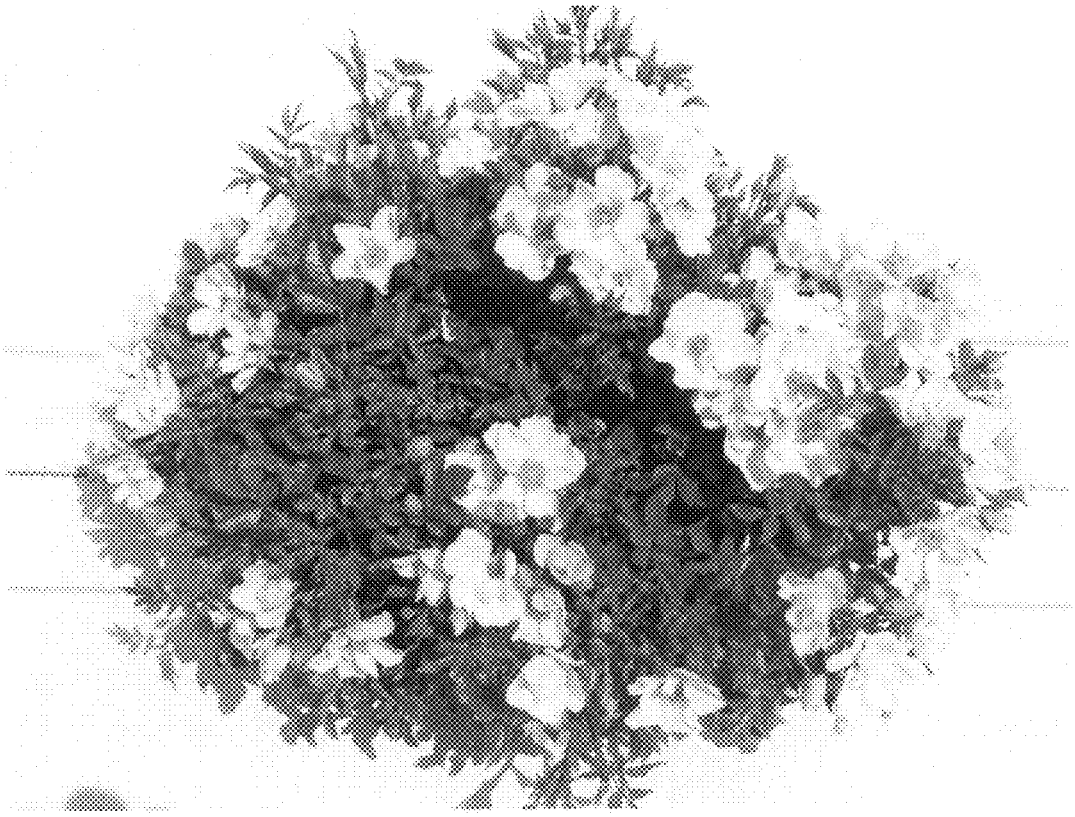
FIG. 2 shows primarily from above another flowering plant wherein the compact, round, and bushy growth habit is well apparent.

The chart used in the identification of the colors is that of The Royal Horticultural Society (R.H.S. Colour Chart) except where ordinary color terms are utilized. Such common color terms are to be accorded their customary dictionary significance. The description is based upon the observation of a plant of the new variety at an age of approximately four years during the month of July while being grown outdoors near West Grove, Pa., U.S.A.

Class: Mini Shrub Rose.

Plant:

*Growth habit.*—Compact, generally round, and bushy.

*Blooming habit.*—Substantially continuous.

*Height.*—Commonly approximately 30 to 50 cm at an age of four years.

*Width.*—Commonly approximately 50 cm at an age of four years.

Branches:

*Length.*—Commonly approximately 8 to 10 cm on average at the end of the season.

Diameter.—Commonly approximately 2 to 3 mm on average at the end of the season.

*Color.*—Young stems: commonly near Yellow-Green Group 146C and Greyed-Orange Group 174A. Adult wood: commonly Greyed-Purple Group 184B with Yellow-Green Group 145A at leaf nodes.

*Thorns.*—Size: commonly approximately 0.3 cm in length, less than 0.1 mm in width towards the apex, and approximately 0.2 cm in width at the base. Color: commonly near Greyed-Orange Group 165A.

Leaves:

*Size.*—Length: commonly approximately 3 cm on average for a five-leaflet leaf. Width: commonly approximately 2 cm on average for a five-leaflet leaf.

*Leaflets.*—Number: 3, 5, and 7. Shape: generally ovate with an acuminate tip and a rounded base. Serration: double serrate. Texture: smooth on both surfaces with a coarse midrib on the under surface. Size: Approximately 2 cm in length, and 1 cm in width for a terminal leaflet, and approximately 1 cm in length and 7 mm in width for a lower leaflet. Color: near Green Group 137C on the upper surface, and near Yellow-Green Group 146C on the under surface.

Inflorescence:

*Bearing.*—Commonly in clusters.

*Peduncle.*—Commonly approximately 2 cm in length on average, approximately 1 mm in width on average, and near Yellow-Green Group 144A in coloration.

*Sepals.*—Number: 5. Shape: acuminate. Length: commonly approximately 1.5 cm on average. Width: commonly approximately 4 mm on average at the base. Apex: aristate. Margins: generally smooth. Texture: smooth and glaucous on the upper surface, and smooth on the under surface. Color: near Green Group 138B on the upper surface, and near Green Group 138C on the under surface.

*Buds.*—Shape: pointed. Length: approximately 1.5 cm on average. Width: approximately 1 cm at the widest point on average. Color as calyx breaks: commonly near Red Group 48D.

*Flower.*—Shape: single and informal. Diameter: aproximately 3 cm on average. Depth: approximately 1 cm on average. Color (newly opened): upper surface: Red Group 38C at the apex fading to Red Group 36B as maturity progresses, and Yellow Group 12C at the base. Under surface: Red Group 49A fading to Red Group 49C as maturity progresses, and Yellow Group 11B at the base. Color (when blooming): upper surface: Red Group 36D. Under surface: Red Group 36D. Color stability: color lightens with advancing maturity. Color (when fully mature): upper surface: Yellow-White Group 158C. Under surface: Yellow-White group 158C. Fragrance: slight. Petal number: approximately 10 on average under normal growing conditions. Petal shape: commonly flat to slightly cupped. Petal length: commonly approximately 1 cm on average. Petal width: commonly approximately 8 mm on average. Petal apex: generally rounded. Petal base: attenuate. Petal margin: smooth. Petal arrangement: slightly imbricated and in a whorl. Petal drop: the petals commonly drop cleanly without drying. Stamen number: approximately 85 to 90 on average. Anthers: regularly arranged around the styles, and near Yellow-Orange Group 17C in coloration. Filaments: commonly approximately 3 to 5 mm on average in length, and near Yellow-Orange Group 17C in coloration. Pistils: separate and free, and approximately 20 on average. Styles: commonly near Yellow-White Group 158B in coloration. Stigmas: commonly near Yellow-White Group 158B in coloration. Hips: during observations to date no hips have been observed.

Development:

*Vegetation.*—Strong and vigorous.

*Blooming.*—Abundant and substantially continuous.

*Tolerance to diseases.*—Above average for Black Spot.

I claim:

1. A new and distinct Mini Shrub Rose plant characterized by the following characteristics:

(a) displays a small low-growing, round, and bushy growth habit, (b) forms vigorous vegetation, (c) forms on a substantially continuous basis attractive single blossoms that are light pink to white in coloration, (d) displays attractive light green foliage having a matte finish, (e) displays above average disease resistance to Black Spot, and (f) is particularly well suited for providing attractive ornamentation; substantially as shown and described.

* * * * *